United States Patent

Ito et al.

Patent Number: 5,117,064
Date of Patent: May 26, 1992

[54] METHOD FOR SYNTHESIZING AROMATIC AMINES, AROMATIC ALCOHOLS AND AROMATIC THIOLS BY AROMATIC NUCLEOPHILIC SUBSTITUTION REACTION

[75] Inventors: Takayuki Ito; Koki Nakamura, both of Kanagawa, Japan

[73] Assignee: Fuji Photo Film Co., Ltd., Kanagawa, Japan

[21] Appl. No.: 645,861

[22] Filed: Jan. 25, 1991

[30] Foreign Application Priority Data

Jan. 25, 1990 [JP] Japan .................. 2-13744

[51] Int. Cl.⁵ .................. C07C 209/14; C07C 213/02
[52] U.S. Cl. .................. 564/399; 564/402; 564/406
[58] Field of Search .................. 564/399, 402, 406

[56] References Cited

U.S. PATENT DOCUMENTS 4,289,907 11/1981 Chan .................. 564/399
4,364,875 12/1982 Sehring .................. 564/399

Primary Examiner—Robert T. Bond
Assistant Examiner—Y. N. Gupta
Attorney, Agent, or Firm—Sughrue, Mion, Zinn Macpeak & Seas

[57] ABSTRACT

A method for synthesizing an aromatic amine, an aromatic alcohol or an aromatic thiol by an aromatic nucleophilic substitution reaction is disclosed, which comprises reacting a compound represented by formula (I):

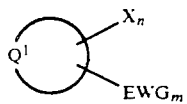

(I)

wherein $Q^1$ represents an aromatic ring; EWG represents a group having a positive Hammett's $\sigma_p$ value; m represents an integer of 1 to 5; n represents an integer of 1 to 3; and X represents a group represented by formula (III):

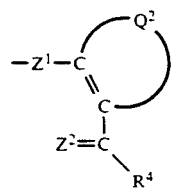

(III)

wherein $R^4$ represents hydrogen atom, an aryl group or an alkyl group; $Q^2$ represents an atomic group for forming an aromatic ring; and $Z^1$ and $Z^2$ each represents an oxygen atom or a sulfur atom with a nucleophilic reagent represented by formula (II):

$$M-Y \qquad (II)$$

wherein M represents a hydrogen atom, a metal atom or an ammonium; Y represents a $-NHR^1$ group, an $-OR^1$ group, or a $-SR^1$ group; $R^1$ represents a hydrogen atom, an alkyl group, an aryl group, a residue of a heterocyclic ring, a $-NR^2R^3$ group or an $-OR^2$ group; and $R^2$ and $R^3$ each represents a hydrogen atom, an alkyl group, an aryl group or a residue of a heterocyclic ring.

13 Claims, No Drawings

METHOD FOR SYNTHESIZING AROMATIC AMINES, AROMATIC ALCOHOLS AND AROMATIC THIOLS BY AROMATIC NUCLEOPHILIC SUBSTITUTION REACTION

FIELD OF THE INVENTION

The present invention relates to a novel method for synthesizing an aromatic amine derivative, an aromatic alcohol derivative or an aromatic thiol derivative, and more particularly to a method for selectively and efficiently synthesizing an aromatic amine derivative, an aromatic alcohol derivative or an aromatic thiol derivative by an aromatic nucleophilic substitution reaction utilizing the participation of an intramolecular substituent group in the reaction.

BACKGROUND OF THE INVENTION

The importance of aromatic amine derivatives, aromatic alcohol derivatives or aromatic thiol derivatives is well known in the chemical industry. Many derivatives of these compounds, particularly those employed in the field of fine chemicals such as medicines, agricultural chemicals, dyes, photographic materials, etc. have complicated structures, and efficient and highly selective synthesis methods thereof are in demand.

Among the aromatic amine derivatives, aniline derivatives are particularly important, and synthesis methods thereof are described in the literature in detail. For example, known synthesis methods include a method wherein the aniline derivative is synthesized by the nitration and reduction of a benzene derivative, a method wherein reduction is carried out after the diazo coupling of a phenol, a method wherein reduction is carried out after forming a nitroso compound of a phenol, a method wherein an aniline derivative is synthesized from an amine and a benzene derivative by aromatic nucleophilic substitution reaction, a method utilizing the rearrangement reaction of a benzoic acid amide derivative and a method utilizing the rearrangement reaction of an acetophenone oxime derivative.

Among the aromatic alcohols, phenol derivatives are most important. Many methods are known for synthesizing a phenol derivative including a method of alkali fusion of an arylsulfonic acid, a method utilizing the rearrangement reaction of an acylbenzene with a peracid, a method wherein a phenol derivative is synthesized from a halobenzene and a hydroxyl ion by an aromatic nucleophilic substitution reaction and a method using the solvolysis of a diazonium salt.

With regard to thiophenols, known synthesis methods include a method wherein a thiophenol is synthesized by the reaction of a halobenzene with hydrogen sulfide ion or functional equivalent thereof through an aromatic nucleophilic substitution reaction, a method using a reduction reaction of an arylsulfonyl halide and a method wherein after a sulfenyl halide is subjected to Friedel-Crafts reaction, a deblocking reaction is carried out by an appropriate method.

Among these reactions, reactions for introducing an amino group, a hydroxyl group or a mercapto group by utilizing an aromatic nucleophilic substitution reaction are often used, because the reactions are generally applicable to aromatic rings having relatively complicated substituent groups. In these reactions, an amine is used when an amino group is introduced, a hydroxyl ion is used when a hydroxyl group is introduced, and a hydrogen sulfide ion is used when a mercapto group is introduced.

However, these reactions are generally carried out under basic conditions and must sometimes be carried out under severe reaction conditions such as under pressure. Hence, when functional groups such as an alkoxycarbonyl group, cyano group, etc. are present which are reactive under basic conditions, it is often necessary that these functional groups are previously protected or temporarily converted into other functional groups, or the reaction by nucleophilic substitution must be stopped.

In the case where two or more reaction sites exist, it is often difficult to selectively introduce a desired group into a desired position when an amine, hydroxyl ion or hydrogen sulfide ion is used.

For this reason, a protected amino group such as phthalimide, benzenesulfonamido group, etc. is used when an amino group is to be introduced. When a hydroxyl group is to be introduced, a protected hydroxyl group such as a carboxylic acid, e.g., acetic acid, or an alcohol such as methanol, etc. is used. When a mercapto group is to be introduced, a protected mercapto group such as xanthic acid, a thiourea, etc. is used.

However, a lowering in pKa particularly results when the protected amino group or the protected hydroxyl group is used to introduce an amino group or a hydroxyl group by the above described method, and in some circumstances, more severe reaction conditions are required. Accordingly, problems are still encountered when functional groups are present which can not withstand the above described basic conditions or which react with the protected amino groups or the protected hydroxyl groups, which protected groups are nucleophilic reagents.

Accordingly, a method has been desired for introducing the above described functional groups under reaction conditions which are as mild as possible.

SUMMARY OF THE INVENTION

A first object of the present invention is to provide an aromatic nucleophilic substitution reaction wherein an amino group, a hydroxyl group or a mercapto group is introduced under mild conditions.

A second object of the present invention is to provide an aromatic nucleophilic substitution reaction wherein an amino group, a hydroxyl group or a mercapto group is selectively introduced when two or more reaction sites exist.

A third object of the present invention is to provide a method for simply and efficiently synthesizing an aromatic amine, an aromatic alcohol or an aromatic thiol by selectively introducing an amino group, a hydroxyl group or a mercapto group under mild conditions.

The present inventors have made studied methods for introducing an amino group, a hydroxyl group or a mercapto group by an aromatic nucleophilic reaction, and particularly to develop (i) a reaction for introducing an amino group, a hydroxyl group or a mercapto group into compounds such as esters or nitriles which are reactive with nucleophilic species, and (ii) a reaction for enabling an aromatic ring substituted by one or more groups which are readily eliminated to be selectively substituted by an amino group, a hydroxyl group or a mercapto group in an aromatic nucleophilic reaction of an alkoxy group, an aryloxy group, an alkylthio group, an arylthio group, a halogen atom (fluorine, chlorine, bromine, iodine), etc.

As a result, the present inventors have discovered that the above-described objective are achieved by providing a method for synthesizing an aromatic amine, an aromatic alcohol or an aromatic thiol by an aromatic nucleophilic substitution reaction, which comprises reacting a compound represented by formula (I):

wherein $Q^1$ represents an aromatic ring; EWG represents a group having a positive Hammett's $\sigma p$ value; m represents an integer of 1 to 5; n represents an anteger of 1 to 3; and X represents a group represented by formula (III):

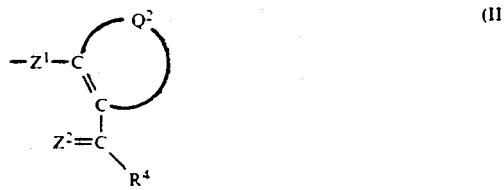

wherein $R^4$ represents a hydrogen atom, an aryl group or an alkyl group; $Q^2$ represents an atomic group for forming an aromatic ring; and $Z^1$ and $Z^2$ each represents an oxygen atom or a sulfur atom, with a nucleophilic reagent represented by formula (II)

wherein M represents a hydrogen atom, a metal atom or an ammonium group; Y represents a —$NHR^1$ group, an —$OR^1$ group, or a —SRl group; $R^1$ represents a hydrogen atom, an alkyl group, an aryl group, a residue of a heterocyclic ring, —$NR^2R^3$ or —$OR^2$; and $R^2$ and $R^3$ each represents a hydrogen atom, an alkyl group, an aryl group or a residue of a heterocyclic ring.

DETAILED DESCRIPTION OF THE INVENTION

One aspect of the present invention is that an amino group, a hydroxyl group or a mercapto group are not introduced directly into an aromatic ring. Rather, in accordance with the present invention, a compound substituted by a phenol or a thiophenol capable of being introduced into an aromatic ring under mild conditions, is first formed and then reacted with a compound having a desired functional group corresponding to amino group, hydroxyl group or the like, to thereby obtain an aromatic ring having the desired functional group at the desired position.

Another aspect of the present invention is that although a phenol or a thiophenol is previously introduced into a position where aromatic nucleophilic substitution is carried out as described above, the 2-position of the phenol or thiophenol is substituted by an electrophilic group such as a carbonyl group or a thiocarbonyl group. An essential characteristic of the present invention resides in this second aspect. As shown in the following reaction scheme, it is considered that the addition of a nucleophilic reagent to the substituent group at the 2-position is first carried out. A lone electron pair of the nucleophilic reagent carried into the molecule from the outside or a lone electron pair formed from an electrophilic center by the addition of the nucleophilic reagent is then added to the position where aromatic nucleophilic substitution is carried out to thereby form a 6-membered Meisenheimer complex intermediate (A) or (B). The Meisenheimer complex is decomposed to thereby obtain the desired compounds. Namely, the present invention is characterized in that a nucleophilic species in the aromatic nucleophilic substitution is newly formed by an intermolecular reaction.

Not to be limited to any particular theory, it is considered that the reaction mechanism of the present invention is as follows. For convenience, the case where n=1 is illustrated.

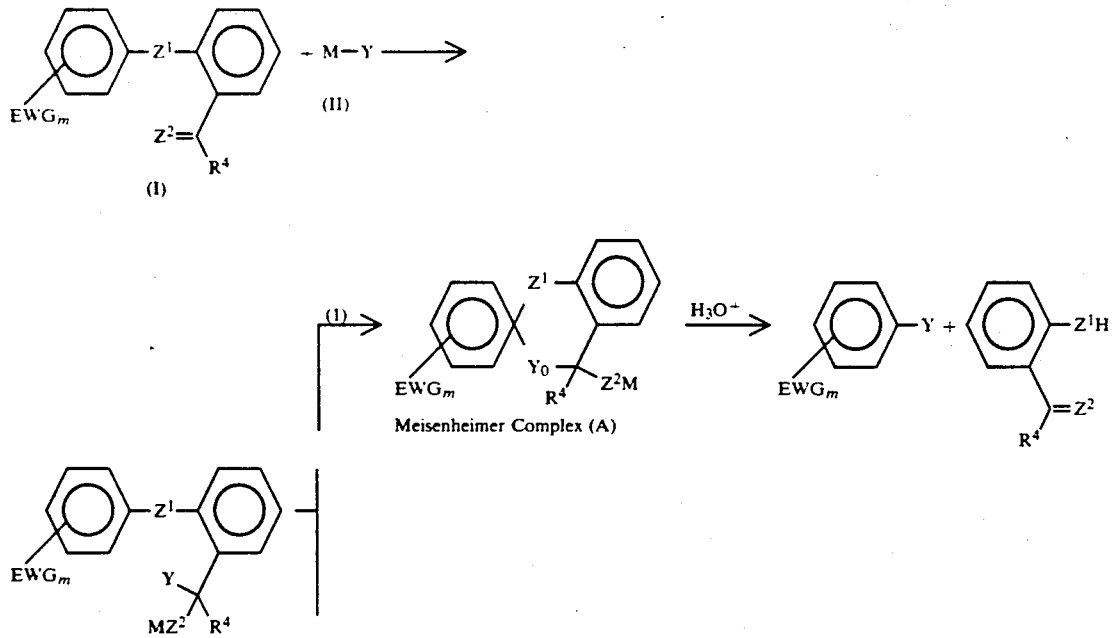

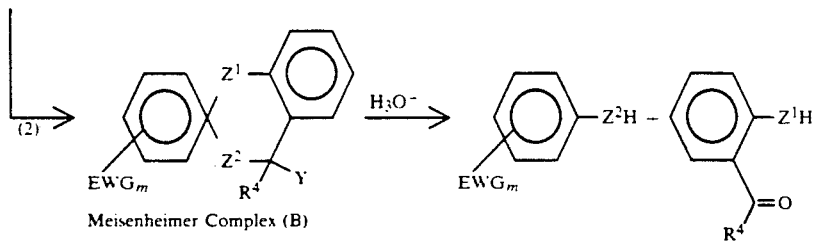

Meisenheimer Complex (B)

In the above-described reaction scheme, the route (1) is the case where Y is a —NHR$^1$ group, an —OH group or a —SH group. In Meisenheimer complex (A), Yo is —NR$^1$—, —O— or —S—, with the exception that when Z$^2$ and Y are —S— and —OH group, respectively, the reaction proceeds via the route (2). On the other hand, the route (2) is the case where Y is a —OR$^1$ group or a —SR$^1$ group excepting the case where a R$^1$ is a hydrogen atom.

It was found that when Y is a secondary amine (e.g., a —NR$^2$ group), the reaction proceeds very slowly in comparison with the case where Y is a primary amine in the above-described reaction.

Furthermore, when n is 2 or 3, all -X groups can be finally substituted by —Y groups or —Z$^2$H groups according to the above-described reaction scheme.

A Smiles rearrangement is known as a reaction similar to the aromatic nucleophilic substitution reaction via said 6-membered Meisenheimer complex. In a Smiles rearrangement, the nucleophilic species is an intramolecular nucleophilic lone electron pair. On the other hand, a novel feature of the present invention resides in that a fresh nucleophilic species is newly formed by an intermolecular nucleophilic addition reaction. This aspect of the present invention provides a number of advantages.

A first advantage provided by the formation of fresh nucleophilic species by the nucleophilic addition reaction is that a nucleophilic reagent can be arbitrarily chosen, because the nucleophilic agent is provided from an external source. A second advantage is that according to the method of the present invention, a desired product is directly obtained without having to remove a protect group, while in a Smiles rearrangement, a step of removing a protect group is generally required to obtain the desired product. A third advantage is that a primary amine is readily discriminated from secondary and tertiary amines according to the method of the present invention, because the primary amine is reacted in the present invention, while the secondary and tertiary amines are not reacted (generally, it is difficult to discriminate the primary amine from the secondary amine in an aromatic nucleophilic substitution reaction.

The rate-determining step is generally an intermolecular nucleophilic addition reaction in the aromatic nucleophilic substitution reaction. In the method of the present invention, however, this means conversion to an intramolecular reaction. Accordingly, the nucleophilic addition reaction which is a rate-determining step becomes an intramolecular reaction such that a reaction rate higher than that of the case where a fluorine atom is eliminated is obtained, which fluorine atom is considered to be the most active in the intermolecular reaction. Thus, in accordance with the present invention, it is possible to carry out a reaction under very mild conditions even when said reaction proceeds slowly, such that the reaction must be carried out at an elevated temperature, optionally under elevated pressure.

The present invention is illustrated in detail below.

In formula (I), Q$^1$ is an aromatic ring. Preferred examples of the aromatic ring are benzene ring, naphthalene ring, pyridine ring, pyrimidine ring, pyrazine ring, triazine ring, furan ring, pyrrole ring, thiophene ring, imidazole ring and triazole ring. Benzene ring and naphthalene ring are more preferred. The aromatic ring represented by Q$^1$ may be further condensed with a saturated or unsaturated ring or rings. Q$^1$ may be substituted with substituents (R$^{11}$)$_l$, wherein R$^{11}$ represents a group other than EWG and X, and l represents a positive integer, with the proviso that m plus l is an integer of 1 to 5. In this case, the total number of Hammett's $\sigma$p values of the substituents (i.e., (R$^{11}$)$_l$ and EWG$_m$) except for X$_n$ is preferably 0.7 or more.

EWG is a substituent group having a positive value of Hammett's $\sigma$p value. Examples of EWG include an electron attractive group or an atom. Examples of useful electron attractive group or atom include a nitro group, a nitroso group, a cyano group, a carboxyl group, a isocyano group, a halogen atom (e.g., fluorine, chlorine, bromine, iodine), an iodosyl group, an iodyl group, a diazo group, an azido group, an acyl group (which may be substituted; e.g., acetyl group, propionyl group, butyroyl group, iso-butyroyl group, 2,2-dimethylpropionyl group, benzoyl group, 3,4-dichlorobenzoyl group, 3-acetylamino-4-methoxybenzoyl group, 4-methylbenzoyl group, etc.), a sulfonyl group (which may be substituted; e.g., methanesulfonyl group, ethanesulfonyl group, chloromethanesulfonyl group, propanesulfonyl group, butanesulfonyl group, n-octanesulfonyl group, n-dodecanesulfonyl group, n-hexadecanesulfonyl group, benzenesulfonyl group, 4-toluenesulfonyl group, 4-n-dodecyloxybenzenesulfonyl group, etc.), a carbamoyl group (which may be substituted; e.g., carbamoyl group, methylcarbamoyl group, dimethylcarbamoyl group, bis-(2-methoxyethyl)carbamoyl group, diethylcarbamoyl group, cyclohexylcarbamoyl group, di-n-octylcarbamoyl group, 3-dodecyloxypropylcarbamoyl group, hexadecylcarbamoyl group, 3-(2,4-di-t-pentylphenoxy)propylcarbamoyl group, 3-octanesulfonylaminophenylcarbamoyl group, di-n-octadecylcarbamoyl group, etc.), a sulfamoyl group (which may be substituted; e.g., sulfamoyl group, methylsulfamoyl group, dimethylsulfamoyl group, bis-(2-methoxyethyl)sulfamoyl group, diethylsulfamoyl group, di-n-butylsulfamoyl group, methyl-n-octylsulfamoyl group, n-hexadecylmethylsulfamoyl group, 3-ethoxypropylmethylsulfamoyl group, N-phenyl—N-methylsulfamoyl group, 4-decyloxyphenylsulfamoyl group, methyloctadecylsulfamoyl group, etc.), an alkoxycarbonyl group (which may be substituted; e.g., methoxycarbonyl group, ethoxycarbonyl group, dodecyloxycarbonyl group, 2-methoxyethoxycarbonyl group, etc.) and an aryloxycarbonyl group (which may be substituted; e.g., phenoxycarbonyl group, 4-nitrophenoxycarbonyl group, 2-methoxyphenoxycarbonyl group, etc.). Those having from 1 to 10 carbon atoms are preferred. A nitro group, a cyano group, a sulfonyl group, an acyl group, a sulfamoyl group and an alkoxycarbonyl group which have from 1 to 10 carbon atoms are more preferred.

In formula (I), m is preferably an integer of 1 to 5 and at least one of the EWG groups is preferably selected from the group consisting of a nitro group, a cyano group, a sulfonyl group, an acyl group, a sulfamoyl group and an alkoxycarbonyl group. When m is a integer of 2 or more, the two or more EWG groups may be the same or different.

X is a group represented by formula (III), which is eliminated in the aromatic nucleophilic substitution reaction.

In formula (III), $R^4$ is a hydrogen atom, an aryl group or an alkyl group. Examples of the aryl group include unsubstituted and substituted aryl groups such as phenyl group, naphthyl group, 3-chlorophenyl group, 2-methanesulfonyl-4-nitrophenyl group, 3-nitrophenyl group, 4-methoxyphenyl group, 4-acetylaminophenyl group, 4-methanesulfonylphenyl group, 2,4-dimethylphenyl group and 4-tetradecyloxyphenyl group. The aryl groups having from 1 to 10 carbon atoms are preferred. Examples of the alkyl group include unsubstituted and substituted alkyl groups such as methyl group, trifluoromethyl group, benzyl group, chloromethyl group, ethoxycarbonylmethyl group, ethyl group, carboxyethyl group, allyl group, n-propyl group, n-butyl group, isobutyl group, n-pentyl group and n-octyl group. The alkyl groups having from 1 to 10 carbon atoms are preferred.

n in formula (I) is an integer of 1 to 3, preferably 1.

$R^4$ is preferably a hydrogen atom.

$Q^2$ is an atomic group for forming an aromatic ring. The aromatic ring include the same rings and condensed structures as defined for the aromatic ring $Q^1$ above. Preferred examples of the aromatic group formed with $Q^2$ are benzene ring and naphthalene ring. The aromatic group formed with $Q^2$ may be substituted. Preferred substituents are a halogen atom (e.g., fluorine, chlorine, bromine and iodine), and an alkyl group, an aryl group, and an alkyloxy group which have from 1 to 10 carbon atoms.

In formula (II), Y is a $-NHR^1$ group, an $-OR^1$ group or a $-SR^1$ group. $R^1$ is a hydrogen atom, an alkyl group, an aryl group, a residue of a heterocyclic ring, a $-NR^2R^3$ group or an $-OR^2$ group. $R^1$ is preferably an alkyl group and an aryl group. Those having from 1 to 20 carbon atoms, particularly from 1 to 10 carbon atoms are preferred.

More specifically, examples of $R^1$ include a hydrogen atom, an alkyl group (including a substituted alkyl group; e.g., methyl group, trifluoromethyl group, benzyl group, chloromethyl group, ethoxycarbonylmethyl group, ethyl group, carboxyethyl group, allyl group, n-propyl group, n-butyl group, isobutyl group, n-pentyl group, n-octyl group, etc.), an aryl group (including a substituted aryl group; e.g., phenyl group, naphthyl group, 3-chlorophenyl group, 2-methanesulfonyl-4-nitrophenyl group, 3-nitrophenyl group, 4-methoxyphenyl group, 4 acetylaminophenyl group, 4-methanesulfonylphenyl group, 2,4-dimethylphenyl group, 4-tetradecyloxyphenyl group, etc.), and a residue of a heterocyclic ring (including a residue of a substituted heterocyclic ring; e.g., 2-imidazolyl group, 2-pyridyl group, 3-pyridyl group, 2-benzoxazolyl group, etc.).

Further, $R^1$ itself may be a $-NR^2R^3$ or an $-OR^2$ group. $R^2$ and $R^3$ each represents a hydrogen atom, an alkyl group, an aryl group or a residue of a heterocyclic ring. Examples of these groups include those described above in the definition of $R^1$.

M is a hydrogen atom, a metal atom or an ammonium group. The ammonium group represented by $(R^{12})_4N+$. Wherein $R^{12}$ represents a hydrogen atom or an alkyl group is preferred. Examples thereof include ammonium, methyl ammonium, diethyl ammonium, tetramethyl ammonium and tetrabutyl ammonium. As the ammonium group, a quaternary ammonium group is more preferred.

Preferred examples of the metal atom include lithium, sodium, magnesium, calcium, silver and copper.

General synthesis methods for use in the present invention are described below.

The compounds represented by formula (I) of the present invention can be synthesized by various known methods.

In the present invention, it is necessary that the X group of formula (III) be introduced into a position on the aromatic ring, into which the amino group, hydroxyl group or mercapto group is introduced. For example, methods for obtaining the compound represented by formula (I) can be roughly classified into the following three methods. (In each of the following reaction schemes, the case where the aromatic ring corresponding to $Q^1$ and $Q^2$ is a phenyl group as a matter of convenience, is illustrated.) (I) A first method (Scheme I) is wherein an aromatic halide (general formula (IV)) which has a halogen atom at a position where an amino group, etc. is to be introduced and which is active with respect to the aromatic nucleophilic reaction, is reacted with a compound represented by the following formula (V) (e.g., salicylaldehyde) in an aprotic solvent under basic conditions.

In formula (IV), Hal is a halogen atom (preferably a fluorine atom or a chlorine atom). $Z^1$, $Z^2$, $R^4$, EWG and m are as defined above.

(Scheme I)

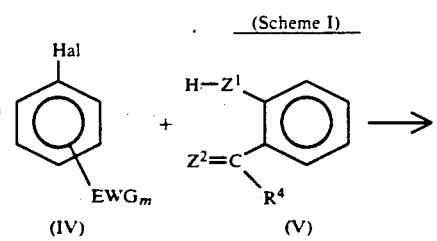

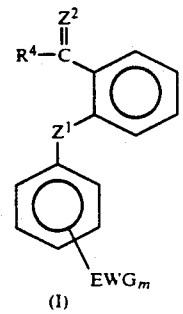

(II) A second method (Scheme II) is wherein an aromatic alcohol (formula (VI)) substituted by an electron attractive group having hydroxyl group or mercapto group at a position where amino group, etc. is to be introduced, is reacted with a halide (formula (VII)) which has an acyl group at the 2-position and is active with respect to the aromatic nucleophilic substitution reaction in an aprotic solvent under basic conditions.

In formulae (VI) and (VII), $R^5$ is preferably an electron attractive group (preferably, Hammett's σp value of $R^5$ does not exceed the sum of the Hammett's σp values of EWG) and Hal, $Z^1$, $Z^2$, $R^4$, EWG and m are as defined above.

Viewed from a different aspect, Scheme II is characterized as being a method for converting a

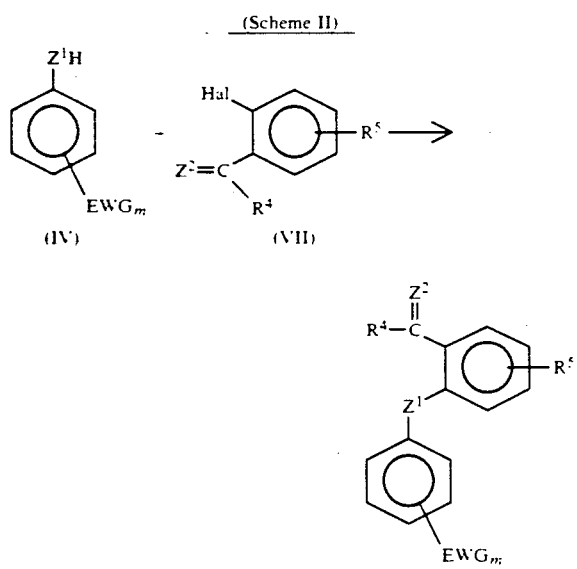

hydroxyl group into other group. The above described method is also valuable from this aspect. (III) A third method (Scheme III) is wherein an aromatic halide (formula (IV)) which has a halogen atom at a position where an amino group, etc. is to be introduced and is active with respect to the aromatic nucleophilic reaction, is reacted with a phenol or thiophenol (formula (VIII); e.g., p-cresol) in an aprotic solvent under basic conditions, and the reaction product is subsequently acylated.

In formula (VIII), $R^6$ is preferably an electron donating group which accelerates the acylation at the ortho-position of the phenoxy or thiophenoxy. Hal, $Z^1$, $Z^2$, $R^4$, EWG and m are as defined above.

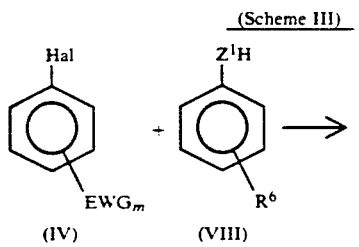

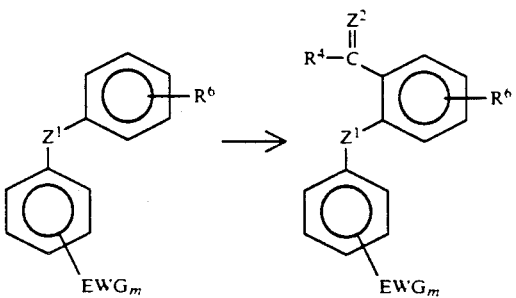

The amination, hydroxylation or mercapto group-forming reaction of a the compounds of general formula (I) obtained as described above is carried out as follows.

(1) Amination

The compound represented by formula (I) are mixed with ammonia gas, ammonia water, an ammonium salt such as ammonium carbonate or a primary amine (in solution or neat) in a protic solvent (e.g., methanol, ethanol, isopropanol, etc.), an aprotic solvent (e.g., dimethylformamide, dimethylacetamide, dimethylsulfoxide, acetonitrile, sulfolane, etc.) or a mixed solvent thereof to thereby readily react the same to obtain an aromatic amine derivative. The reaction temperature varies depending on the nucleophilicity of the amino group to be introduced and the types of the compounds of formula (I), but the reaction is preferably carried out at a temperature of from 0 to about 80° C.

(2) Hydroxylation

In the case of hydroxylation, $Z^2$ in the compounds represented by formula (I) is an oxygen atom. The compound is mixed with a base (e.g., sodium hydroxide, potassium hydroxide, alcoholates, etc.) in a protic solvent (e.g., methanol, ethanol, isopropanol, etc.), an aprotic solvent (e.g., formamide, dimethylacetamide, dimethyl sulfoxide, acetonitrile, sulfolane, etc.) or a mixed solvent thereof to thereby readily obtain an aromatic alcohols. A reaction temperature of from 0 to 80° C generally provides good results.

(3) Mercapto Group Formation

The mercapto group forming reaction is carried out in the following manner.

When $Z^2$ in the compounds represented by formula (I) is a sulfur atom, the compound is mixed with a base (e.g., sodium hydroxide, potassium hydroxide, alcoholates, etc.) in a protic solvent (e.g., methanol, ethanol, isopropanol, etc.), an aprotic solvent (e.g., dimethylformamide, dimethylacetamide, dimethyl sulfoxide, acetonitrile, sulfolane, etc.) or a mixed solvent thereof to thereby readily obtain an aromatic thiol.

When $Z^2$ in the compound represented by formula (I) is an oxygen atom, the compound is treated with a compound of formula (II) such as NaHS in a protic solvent (e.g., methanol, ethanol, isopropanol, etc.), an aprotic solvent (e.g., dimethylformamide, dimethylacetamide, dimethyl sulfoxide, acetonitrile, sulfolane, etc.) or in a mixed solvent thereof, to thereby synthesize the desired compound.

In the most cases, any of the above described solvents for use in the present invention allows the reaction to proceed, as long as the substrate compound and the nucleophilic reagent are uniformly dispersed in the reaction system. However, the aprotic solvent is preferable when the reaction is to be carried out under strongly basic conditions.

A reaction temperature of from 0° to 80° C. generally provides good results as described above in the case of amination.

An example of a useful synthesis method in accordance with the present invention includes the synthesis of aniline (compound C) as described below. Namely, when the following compound A is reacted with ammonia or p-toluenesulfonamide, these nucleophilic reagents are substituted for the alkoxy group. When phthalimide is used as the nucleophilic reagent, a compound is obtained where phthalimide anion is substituted for a chloro group, but the yield is very poor and it is difficult to practically employ such a reaction.

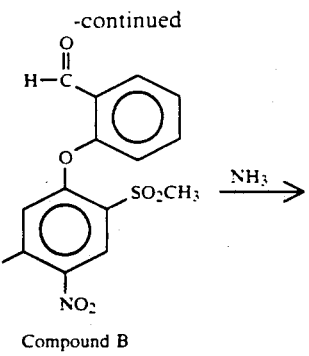

Compound B

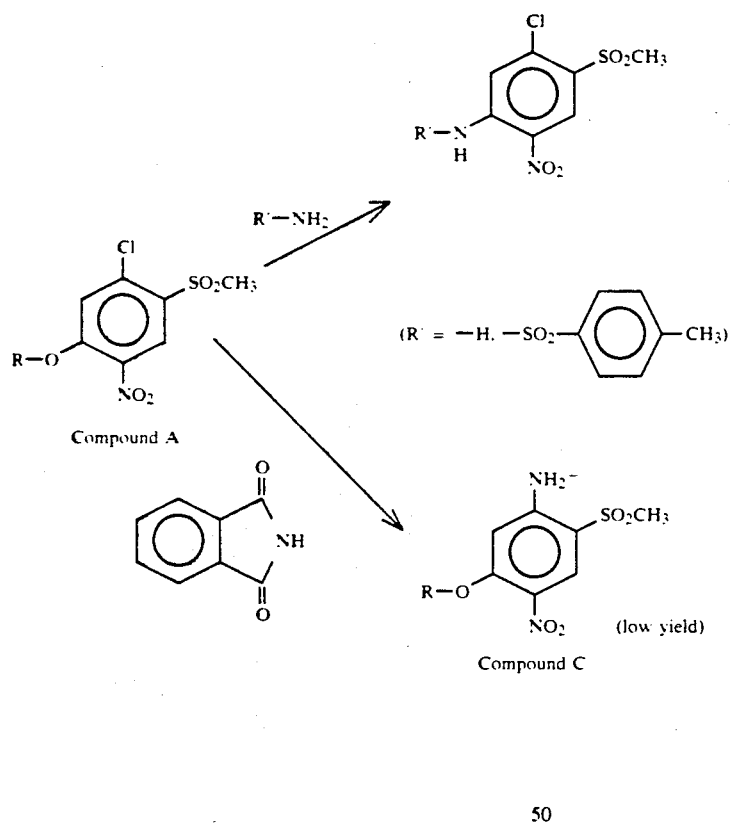

Compound A

Compound C

As an example, according to the method of the present invention, salicylaldehyde is first reacted with the compound A to selectively replace the chloro group, whereby the compound B is obtained. The compound B is readily reacted with ammonia at room temperature to obtain the compound C in high yield.

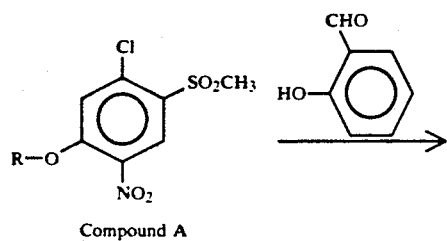

Compound A

Accordingly, the method of the present invention enables positionwise selective amination to be conducted very efficiently, whereas amination is difficultly accomplished using conventional methods.

The present invention is now illustrated in greater detail by reference to the following examples which, however, are not to be construed as limiting the invention in any way.

EXAMPLE 1

Synthesis of 4-nitro-2-methanesulfonyl-5-(2-methoxyethoxy)aniline

According to the method of the present invention, not only is an aromatic nucleophilic reaction readily carried out, and optionally with a degree of selectivity not obtained by conventional methods.

For example, the alkoxy group is selectively replaced according to conventional methods when the amination of the compound D is carried out by the aromatic nucleophilic substitution reaction as illustrated below.

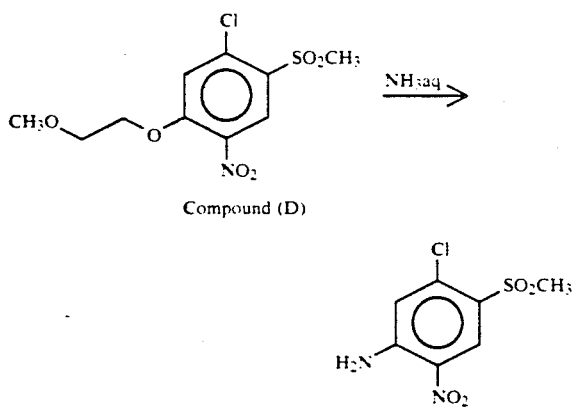

Compound (D)

On the other hand, the replacement of o-formylphenoxy group selectively occurs at the para-position with respect to the nitro group. The aromatic nucleophilic substitution reaction is very accelerated according to the method of the present invention that when the amination is carried out, the alkoxy group at the position-2 against nitro group is not replaced, but the replacement selectively occurs at a position where an o-formylphenoxy group is attached as illustrated below.

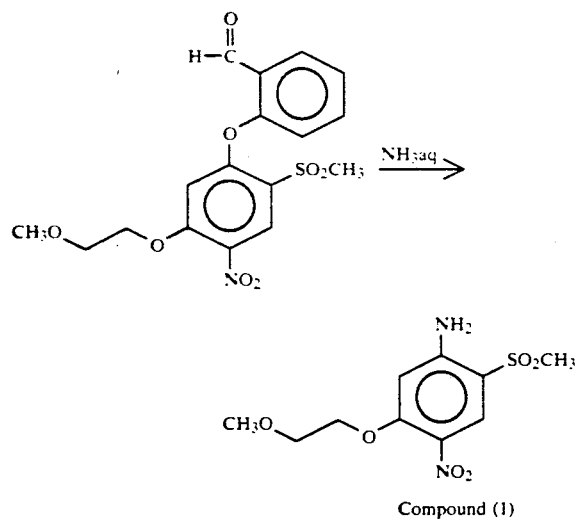

Compound (1)

Compound (1) is useful as a diazo component aniline for an 2-acylamino-1-naphthol azo type cyan dye which is excellent in hue, fastness and solubility.

The synthesis method of 4-nitro-2-methanesulfonyl-5-(2-methoxyethoxy)aniline (compound (1)) is described below.

SYNTHESIS EXAMPLE 1-1

Synthesis of 2,4-dichloromethanesulfonylbenzene

To 0.3 mol of methanesulfonic acid anhydride heated to 85° C. were added 22 g (0.15 mol) of m-dichlorobenzene and 1.5 ml (0.017 mol) of trifluoromethanesulfonic acid. The reaction mixture was heated to 125° C. and stirred at that temperature for 7 hours. Subsequently, the reaction mixture was cooled to 30° C. and then a mixed solution of 300 ml of water and 300 ml of isopropyl alcohol was added dropwise thereto to thereby precipitate a while crystal. The crystal was recovered by filtration and washed with water to obtain 2,4-dichloromethanesulfonylbenzene. Yield: 24 g (72%).

$^1$H NMR(CDCl$_3$)δ68.11(1H, d, J=8.7Hz), 7.10 (1H, d, J=1.3Hz), 7.49(1H, dd, J=8.7Hz), 3.29(3H, s)

SYNTHESIS EXAMPLE 1-2

Synthesis of 2,4-dichloro-5-methanesulfonylnitrobenzene 24 g of 2,4-dichloromethanesulfonylbenzene was dissolved in 133 g of concentrated sulfuric acid. The resulting solution was added dropwise to a mixed acid (nitric acid (d=1.38) 12.4 g/concentrated sulfuric acid 16.3 g) at 20° C. After the mixture was stirred at 20° C. for one hour, the reaction mixture was added dropwise to ml of ice water. The precipitated crystal was recovered by filtration, washed with water and dried to obtain 2,4-dichloro-5-methanesulfonylnitrobenzene. Yield: 28.6 g (99%).

$^1$H NMR(CDCl$_3$) δ8.69(1H, s), 7.81(1H, s), 3.33(3H, s).

SYNTHESIS EXAMPLE 1-3

Synthesis of 2-methoxyethoxy-4-chloro-5-methanesulfonylnitrobenzene

To a mixture consisting of 50 g of 2,4-dichloro-5-methanesulfonylnitrobenzene and 150 ml of methoxyethanol was added dropwise a methoxyethanol solution of potassium hydroxide (potassium hydroxide 14.6 g/methoxyethanol 150 ml) while keeping the temperature at −5° C. or below. The reaction was carried out at −2° C. for 30 minutes and the reaction mixture was neutralized by adding 4 ml of concentrated hydrochloric acid. The neutralized mixture was heated to 90° C, whereby a uniform solution was formed. After the solution was cooled to 70° C., 220 ml of warm water was added dropwise thereto. The resulting precipitated crystal was recovered by filtration and dried to obtain 2-methoxyethoxy-4-chloro-5-methanesulfonylnitrobenzene. Yield: 50 g (87%).

$^1$H NMR(CDCl$_3$) δ8.65(1H, s), 7.36(1H, s), 4.39(2H, t, J=5.3Hz), 3.84(2H, t, J=5.3Hz), 3.48(3H, s), 3.30(3H, s).

SYNTHESIS EXAMPLE 1-4

Synthesis of 4-(2-formyl)phenoxy-5-methanesulfonyl-2-methoxyethoxynitrobenzene

To a mixed solution consisting of 45 g of 4-chloro-5-methanesulfonyl-2-methoxyethoxynitrobenzene, 24.1 g of potassium carbonate and 130 ml of DMF (dimethylformamide), 19.5 ml of salicylaldehyde was added dropwise thereto at room temperature. The reaction mixture was heated to 70° C. and the reaction was carried out for 2 hours. The reaction mixture was cooled to room temperature and slowly added dropwise to a mixed solution consisting of 250 ml of ice water, 50 ml of acetonitrile and 23 ml of concentrated hydrochloric acid, to precipitate a crystal. The crystal was washed with water and dried to obtain 4-(2-formyl)phenoxy-5-methanesulfonyl-2-methoxyethoxynitrobenzene. Yield: 46.7 g (81%).

¹H NMR(CDCl₃) δ10.21(1H, s), 8.69–6.50(6H, m), 4.08(2H, t, J=5.8Hz), 3.69(2H, t, J=5.8Hz), 3.40(3H, s), 3.32(3H, s).

SYNTHESIS EXAMPLE 1-5

Synthesis of 4-nitro-2-methanesulfonyl-5-methoxyethoxyaniline

A DMF solution of 45 g (15.2 mmol) of 4-(2-formyl)-phenoxy-5-methanesulfonyl-2-methoxyethoxynitrobenzene was cooled to 5° C., and 45 ml of a 28% aqueous ammonia solution was added dropwise thereto at such a rate such that the temperature of the reaction mixture did not exceed 20° C.. After the completion of dropwise addition, the temperature of the reaction mixture was elevated to 25° C. and the reaction mixture was stirred for one hour. Subsequently, the temperature was again cooled to 10° C. and 200 ml of water was added dropwise thereto. The thus formed crude crystal was recovered by filtration and then recrystallized from a mixed solution of acetonitrile 50 ml/methanol 50 ml to obtain 4-nitro-2-methanesulfonyl-5-methoxyethoxyaniline. Yield: 28 g (89%).

¹H NMR(CDCl₃) δ8.41(1H, s), 6.75(2H, bs), 6.60(1H, s), 4.22(2H, t, J=5.7Hz), 3.82(2H, t, J=5.7Hz), 3.46(3H, s), 3.10(3H, s).

EXAMPLE 2

Synthesis of 2-cyano-4-methanesulfonylaniline

SYNTHESIS EXAMPLE 2-1

Synthesis of 2-(2-formyl)phenoxy-5-methanesulfonylbenzonitrile

To 20 ml of DMAC (dimethylacetamide) was added 1.0 g of 2-chloro-5-methanesulfonylbenzonitrile, and 0.85 g of salicylaldehyde was then added thereto. Furthermore, 1 g of potassium carbonate was added thereto and the mixture was reacted at 80° C. for 2 hours. The reaction mixture was poured into dilute hydrochloric acid and the precipitated crystal was recovered by filtration. The crystal was recrystallized from a mixed solution of acetonitrile and a small amount of water. Yield: 89%

SYNTHESIS EXAMPLE 2-2

Synthesis of 2-cyano-4-methanesulfonylaniline 1.0 g of 2-(2-formyl)phenoxy-5-methanesulfonylbenzonitrile synthesized in Synthetic Example 2-1 was mixed with 15 ml of DMSO (dimethyl sulfoxide). To the resulting mixture was added 3 g of ammonium carbonate and the mixture was reacted at 60° C. for 1.5 hours. After the completion of the reaction, dilute hydrochloric acid and ethyl acetate were added thereto to carry out extraction. The resulting organic layer was thoroughly washed with water and dried over magnesium sulfate. After the solvent was removed by distillation under reduced pressure, the residue was crystallized from isopropyl alcohol and a small amount of water to obtain 0.5 g of 2-cyano-4-methanesulfonylaniline.

Yield: 95%. Melting point: 155°–157° C.

EXAMPLE 3

Synthesis of 2-chloro-4,5-doicyanoaniline

SYNTHESIS EXAMPLE 3-1

Synthesis of 4-(2-formyl)phenoxy-5-chlorophthalonitrile

To 150 ml of DMAC was added 15 g of 4,5-dichlorophthalonitrile, and 10.2 g of salicylaldehyde was then added thereto. Furthermore, 12.8 g of potassium carbonate was added thereto, and the mixture was reacted at 60° C. for 3 hours. After the completion of the reaction, the reaction mixture was poured into dilute hydrochloric acid and the precipitated crystal was recovered by filtration. The resulting crystal was recrystallized from a mixed solution of ethanol and a small amount of acetonitrile. Yield: 75%.

SYNTHESIS EXAMPLE 3-2

Synthesis of 2-chloro-4,5-dicyanoaniline 2.0 g of 4-(2-formyl)phenoxy-5-chlorophthalonitrile was mixed with 15 ml of DMSO, and 6 g of ammonium carbonate was added thereto. The mixture was reacted at 60° C. for 2 hours. After the completion of the reaction, dilute hydrochloric acid and ethyl acetate were added thereto to conduct extraction. The resulting organic layer was washed with water and then dried over magnesium sulfate. After the solvent was removed by distillation under reduced pressure, the residue was crystallized from isopropyl alcohol and a small amount of water to obtain 1.26 g of 2-chloro-4,5-dicyanoaniline.

Yield: 85%. Melting point: 206°–209° C.

EXAMPLE 4

The following schemes illustrate the synthesis of other compounds according to the method of the present invention. Reaction conditions, yields, products and the melting points of the products are shown in Table 1.

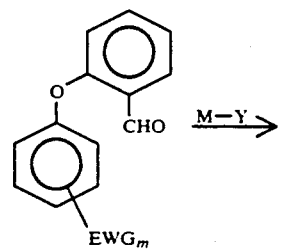

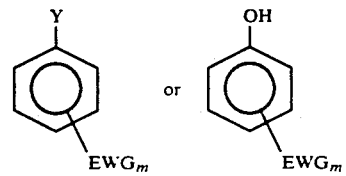

TABLE 1

| Example | X[a]—Q[1]—EWG[m] | Nucleophilic species (equivalent) | Reaction Conditions solvent, temp., time | Yield[b] (%) | Product (MP, °C) |
|---|---|---|---|---|---|
| 4 | 4-nitrophenyl-X | NH₃ aq (10) | DMSO, 50° C., 3.5 hr | 88 | 4-nitroaniline (148–150) |
| 5 | 2-(methylsulfonyl)-4-nitrophenyl-X | NH₃ aq (10) | DMF, 25° C., 1 hr | 93 | 2-(methylsulfonyl)-4-nitroaniline (195–197) |
| 6 | 2-cyano-4-nitrophenyl-X | NH₃ aq (10) | DMF, 25° C., 1 hr | 92 | 2-amino-5-nitrobenzonitrile (206–209) |
| 7 | 5-(2-methoxyethoxy)-2-(methylsulfonyl)-4-nitrophenyl-X | NaSH · H₂O (2.5) | DMF, 25° C., 0.5 hr | 87 | 5-(2-methoxyethoxy)-2-(methylsulfonyl)-4-nitrothiophenol (183–185) |
| 8 | 5-(2-methoxyethoxy)-2-(methylsulfonyl)-4-nitrophenyl-X | NH₂NH₂·H₂O (7) | CH₃CN, 25° C., 1 hr | 75 | 5-(2-methoxyethoxy)-2-(methylsulfonyl)-4-nitrophenylhydrazine (177–179) |
| 9 | 4-nitrophenyl-X | NaOH aq (3) | DMSO, 65° C., 0.3 hr | 89 | 4-nitrophenol (112–115) |
| 10 | 5-(2-methoxyethoxy)-2-(methylsulfonyl)-4-nitrophenyl-X | CH₃ONa (3) | THF, 0° C., 0.5 hr | 75 | 5-(2-methoxyethoxy)-2-(methylsulfonyl)-4-nitrophenol (162–165) |
| 11 | " | CH₃SNa (3) | THF, 0° C., 0.5 hr | 70 | |

[a] —O—C₆H₄—CHO (ortho)
[b] Isolated yield

The following experimental examples are provided to illustrate the unexpected superiority of the present invention.

EXPERIMENTAL EXAMPLE 1

TABLE 2

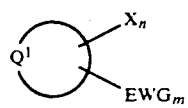

| X | $k_1(\sec^{-1})^{a)}$ | Relative of Reaction Rate$^{d)}$ | |
|---|---|---|---|
| Cl | $8.75 \cdot 10^{-5}$ | 1 | Comp. Ex. |
| o-CHO—C$_6$H$_4$—O— | $1.61 \times 10^{-2}$ | 184 | Invention |
| p-CHO—C$_6$H$_4$—O— | $4.59 \cdot 10^{-5}$ | 0.52 | Comp. Ex. |
| p-O$_2$N—C$_6$H$_4$—O— | $2.15 \cdot 10^{-4}$ | 2.5 | Comp. Ex. |

$^{a)}$Pseudo first-order reaction rate constant when 10 ml of n-BuNH$_2$(1M in CH$_3$CN) are mixed with 10 ml of (A) (0.01M in CH$_3$CN) at 25° C
$^{d)}$Relative reaction rate where X=Cl is given as 1

TABLE 3

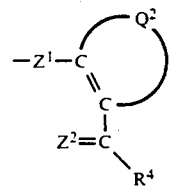

| X | $k_1(\sec^{-1})^{e)}$ | Relative of Reaction Rate$^{f)}$ |
|---|---|---|
| F | $5.64 \cdot 10^{-6}$ | 1 |
| o-CHO—C$_6$H$_4$—O— | $8.64 \cdot 10^{-5}$ | 15.3 |

$^{e)}$Pseudo first-order reaction rate constant when 10 ml of n-BuNH$_2$(1M in CH$_3$CN) is mixed with 10 ml of (B) (0.01M in CH$_3$CN) at 25° C
$^{f)}$Relative reaction rate where X=F is given as 1

The advantages of the present invention are clearly seen from the above-described Experimental Examples 1 and 2. Namely, it is apparent from Experimental Example 1 that when o-formylphenoxy group is first substituted for the halogen atom and the desired nucleophilic reagent is substituted for the o-formylphenoxy group, the desired product is readily obtained by an accelerating effect originating from the o-formyl group in comparison with the case where the nucleophilic reagent is directly substituted for the halogen atom in the aromatic nucleophilic substitution reaction. It is apparent from Experimental Example 2 that when the eliminated group is o-formylphenoxy group, reactivity is high in comparison with the case where the eliminated group is a fluorine atom, even though it is conventionally considered that reactivity is highest when the eliminated group is fluorine atom.

According to the present invention, an amino group, a hydroxyl group or a mercapto group can be introduced into the aromatic ring simply and efficiently under mild reaction conditions.

Furthermore, when two or more reaction sites exist, an amino group, a hydroxyl group or a mercapto group can be selectively introduced into the aromatic ring according to the present invention.

While the invention has bene described in detail and with reference to specific embodiments thereof, it will be apparent to one skilled in the art that various changes and modification can be made therein without departing from the spirit and scope thereof.

What is claimed is:

1. A method for synthesizing an aromatic amine, an aromatic alcohol or an aromatic thiol by an aromatic nucleophilic substitution reaction, which comprises reacting a compound represented by formula (I):

wherein Q$^1$ is a benzene or naphthalene ring; EWG represents a group having a positive Hammett's $\sigma_p$ value; m represents an integer of 1 to 5; n represents an integer of 1 to 3; and X represents a group represented by formula (III):

$$-Z^1-C\underset{Z^2=C}{\overset{Q^2}{\bigcirc}}\!\!\!\!\!\!\!\!\!\!\!\!\!\!-R^4 \qquad (III)$$

wherein R$^4$ represents hydrogen atom, an aryl group or an alkyl group; Q$^2$ represents an atomic group for forming an aromatic ring; and Z$^1$ and Z$^2$ each represents an oxygen atom or a sulfur atom with a nucleophilic reagent represented by formula (II):

$$M-Y \qquad (II)$$

wherein M represents a hydrogen atom, a metal atom or ammonium; Y represents a —NHR$^1$ group, an —OR$^1$ group, or a —SR$^1$ group; R$^1$ represents a hydrogen atom, an alkyl group, an aryl group, a residue of a heterocyclic ring, a —NR$^2$R$^3$ group or an —OR$^2$ group; and R$^2$ and R$^3$ each represents a hydrogen atom, an alkyl group, an aryl group or a residue of a heterocyclic ring.

2. A method as in claim 1, wherein Y in formula (II) is a —NHR$^1$ group, an —OH group or a —SH group.

3. A method as in claim 1, wherein the group EWG of formula (I) is an electron attractive group or atom selected from a nitro group, a nitroso group, a cyano group, a carboxyl group, an isocyano group, a halogen atom, an iodosyl group, iodyl group, a diazo group, an azido group, an acyl group, a sulfonyl group, a carbamoyl group, a sulfamoyl group, an alkoxycarbonyl group, and an aryloxycarbonyl group.

4. A method as in claim 1, wherein the group EWG of formula (I) is selected from a nitro group, a cyano group, a sulfonyl group, an acyl group, a sulfamoyl group and an alkoxycarbonyl group.

5. A method as in claim 1, wherein n is 1.

6. A method as in claim 1, wherein the group represented by R$^4$ of formula (III) is a hydrogen atom.

7. A method as in claim 1, wherein the reaction is carried out at a temperature of from 0°-80° C.

8. A method as in claim 1, wherein a compound represented by formula (I) is reacted with a compound represented by formula (II) selected from ammonium gas, ammonia water, an ammonium salt and a primary amine in a protic solvent, an aprotic solvent or a mixed solvent thereof at a temperature of from 0°-80° C. to obtain an aromatic amine derivative.

9. A method as in claim 1, wherein a compound represented by formula (I) wherein the group $Z^2$ is an oxygen atom is reacted with a base represented by formula (II) in a protic solvent, an aprotic solvent or a mixed solvent thereof at a temperature of from 0°-80° C. to obtain an aromatic alcohol.

10. A method as in claim 1, wherein a compound represented by formula (I) wherein the group $Z^2$ is a sulfur atom is reacted with a base represented by formula (II) in a protic solvent, an aprotic solvent or a mixed solvent thereof at a temperature of from 0°-80° C. to obtain an aromatic thiol.

11. A method as in claim 1, wherein a compound represented by formula (I) wherein the group $Z^2$ is an oxygen atom is reacted with NaHS in a protic solvent, an aprotic solvent or a mixed solvent thereof at a temperature of from 0°-80° C. to obtain an aromatic thiol.

12. A method as in claim 1, wherein the metal atom represented by M in formula (II) is selected lithium, sodium, magnesium, calcium, silver and copper.

13. A method as in claim 1, wherein the ammonium group represented by M of formula (II) is a quaternary ammonium group.

* * * * *